United States Patent [19]

Engel

[11] 4,408,991
[45] Oct. 11, 1983

[54] SELF-CLEANING MIRROR

[76] Inventor: Joseph R. Engel, 835 Hwy. 141, Fenton, Mo. 63026

[21] Appl. No.: 330,190

[22] Filed: Dec. 14, 1981

[51] Int. Cl.³ .................................................. A61B 1/24
[52] U.S. Cl. .......................................... 433/30; 128/21
[58] Field of Search ............... 128/10, 21, 22; 433/31, 433/30

[56] References Cited

U.S. PATENT DOCUMENTS

| 163,578 | 5/1875 | Cogswell | 128/10 |
|---|---|---|---|
| 811,806 | 2/1906 | Walker | 128/10 |
| 1,909,853 | 5/1933 | Dalton | 128/10 |
| 3,102,338 | 9/1963 | Warriner | 433/31 |

FOREIGN PATENT DOCUMENTS

| 681636 | 3/1964 | Canada | 128/21 |
|---|---|---|---|
| 1813003 | 11/1969 | Fed. Rep. of Germany | 128/21 |

Primary Examiner—Kyle L. Howell
Assistant Examiner—Max F. Hindenburg
Attorney, Agent, or Firm—Senniger, Powers, Leavitt and Roedel

[57] ABSTRACT

A self-cleaning mirror comprising a rotor having a shaft, a disc on an end of the shaft, constituting the outer end of the shaft, presenting a reflective surface at its outer face, and a plurality of vanes extending laterally with respect to the shaft. The rotor is mounted for rotation within a housing having an open end with the reflective surface of the rotor being disposed adjacent the open end of the housing. An inlet port directs fluid under pressure from a source thereof against the vanes at an angle causing the rotor to rotate, whereby the rotor expels, by centrifugal force, water or other flowable material which may come into contact with its reflective surface thereby keeping it clean.

9 Claims, 3 Drawing Figures

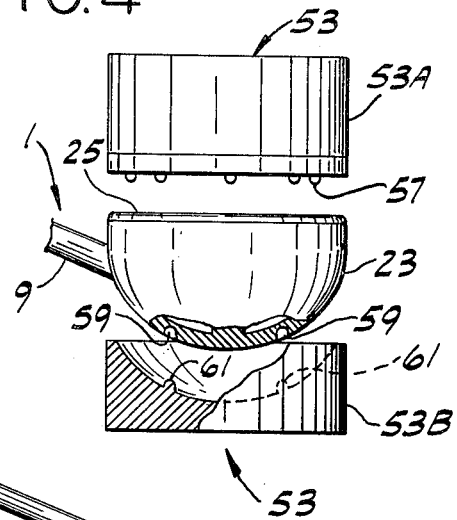
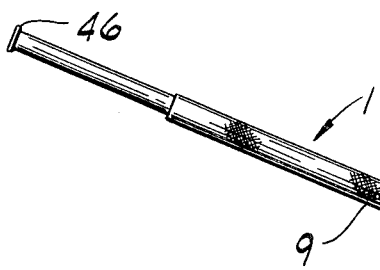
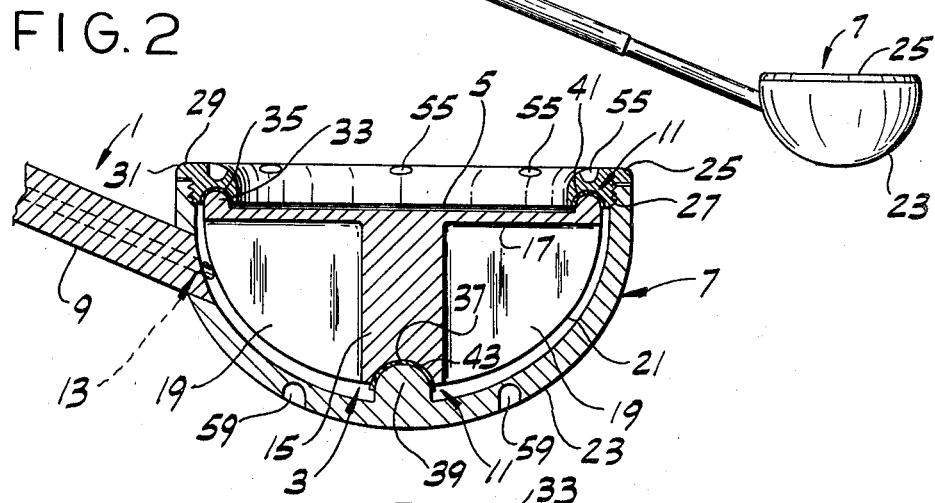
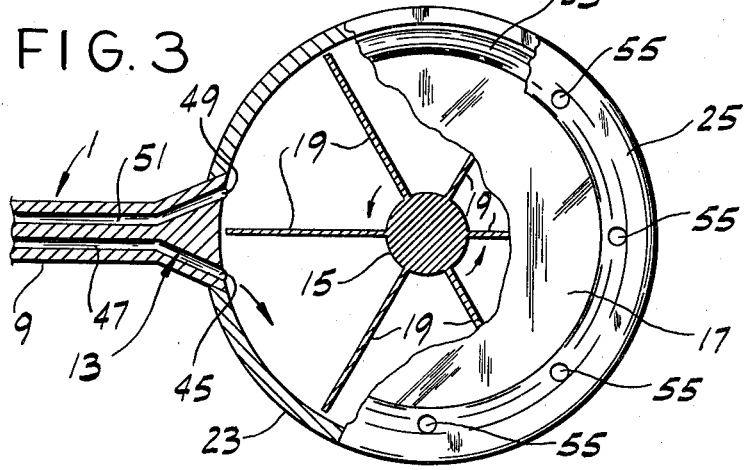

SELF-CLEANING MIRROR

BACKGROUND OF THE INVENTION

This invention relates to a mirror, and more particularly to a self-cleaning mirror for use in dental and surgical procedures.

Mirrors used in dental and surgical procedures are typically exposed to saliva, water, blood and other flowable material which may render their reflecting surfaces wholly or partially non-reflective. To avoid the tedious and time-consuming operation of manually cleaning the mirrors during these procedures, various mirrors having a self-cleaning feature have been proposed. However, the prior art self-cleaning mirrors have not been entirely satisfactory and thus have not become widely used.

Reference may be made to U.S. Pat. No. 3,859,987 disclosing a mirror of this type.

SUMMARY OF THE INVENTION

Among the several objects of this invention may be noted the provision of an improved mirror of the above-noted type in which its reflective surface is rotated to expel, by centrifugal force, water or other flowable material which may come into contact with the reflective surface; the provision of such a mirror in which its rotating parts are enclosed in a manner such as to enable the mirror safely to be used in the oral cavity or other body cavities; the provision of such a mirror in which the area to be viewed is not exposed to the fluid under pressure used to drive the rotating parts of the mirror; the provision of such a mirror in which those of its parts which are subject to wear may be readily replaced; the provision of such a mirror which is relatively compact; and the provision of such a mirror which is economical to manufacture.

In general, the mirror of this invention comprises a rotor having a rotor shaft, a disc on an end of the shaft, constituting the outer end of the shaft, presenting a reflective surface at its outer face, and a plurality of vanes extending laterally with respect to the shaft. A housing having an open end receives the rotor with the reflective surface of the rotor being disposed adjacent the open end of the housing. Bearing means mounts the rotor for rotation within the housing. Means is provided for rotating the rotor comprising an inlet port for the housing for directing fluid under pressure from a source thereof against the vanes at an angle causing the rotor to rotate, whereby the rotor expels, by centrifugal force, water or other flowable material which may come into contact with its reflective surface, thereby keeping it clean.

Other objects and features of this invention will be in part apparent and in part pointed out hereinafter.

BRIEF DESCRIPTION OF THE DRAWINGS

FIG. 1 is a side elevation of a self-cleaning mirror of this invention;

FIG. 2 is an enlarged longitudinal central section of the mirror with a portion of a handle of the mirror broken away;

FIG. 3 is an enlarged top plan of the mirror with a portion of the handle broken away and with other portions broken away to show interior detail; and FIG. 4 is an enlarged side elevation of the mirror and a pair of tools for assembling and disassembling it.

Corresponding reference characters indicate corresponding parts throughout the several views of the drawings.

DESCRIPTION OF THE PREFERRED EMBODIMENT

Referring to FIGS. 1-3, there is generally indicated at 1 a mirror of this invention for use in dental procedures comprising a rotor 3 presenting a generally planar reflective surface 5 at its outer face, and a housing 7 having an open end receiving the rotor with its reflective surface disposed adjacent the open end of the housing. The housing has a handle 9 by which the dentist or his assistant may hold the mirror during the dental procedure. Bearing means indicated generally at 11 mounts the rotor for rotation within the housing. As described more fully hereinafter, means indicated generally at 13 rotates the rotor at a relatively high speed, whereby the rotor expels, by centrifugal force, water or other flowable material which may come into contact with its reflective surface 5, thereby keeping it clean.

The rotor 3 is formed, as by a conventional molding process such as injection molding, of a suitable synthetic plastic material adapted to withstand sterilizing temperatures in an autoclave. The rotor is relatively inexpensive to manufacture and thus is intended to be replaced whenever it becomes worn or its reflective surface 5 becomes marred. As best illustrated in FIGS. 2 and 3, the rotor comprises a cylindrical shaft 15, a disc 17 on an end of the shaft constituting its outer end, and a plurality of vanes 19 at spaced intervals around the shaft extending laterally outwardly from the shaft. The outer face of the disc 17 is coated with a highly reflective material thereby presenting the stated reflective surface 5. The reflective surface 5 is shown in FIG. 2 to be flat, but it may also be made slightly concave or convex depending upon the intended use of the mirror. Each vane 19 is integrally formed with the shaft 15 and the disc 17, and extends laterally outwardly from the shaft to an outer edge 21 which is spaced inwardly of the inner surface of the housing 7.

The housing 7 is formed of a suitable material such as stainless steel and comprises a generally bowl-shaped member or cup 23 of generally shallow profile to which the handle 9 is secured, and a retaining ring 25 for holding the rotor in the cup. The interior of the cup at its open end and the ring at its periphery are threaded as indicated at 27 for detachably securing the ring to the cup. The ring projects radially beyond its threaded portion to form an annular lip 29 having a rounded peripheral edge 31 which is flush with the outer surface of the cup, thereby giving the housing 7 a smooth, finished appearance. As shown in FIG. 2, the ring 25 extends over the reflective surface 5 thereby preventing, at least to some extent, the engagement of the reflective surface with the patient's teeth or other dental instruments in the patient's mouth which could cause marring of the reflective surface.

The bearing means 11 comprises an annular ridge or tongue 33 on the outer face of the disc 17 at the edge margin thereof, and an annular recess or groove 35 in the inner face of the retaining ring which receives the ridge. It further comprises a generally hemispherical recess 37 in the inner end of the rotor shaft, and a projection or 39 complementary in shape to the recess 37 at the center of the inner surface of the cup. With the ring 25 threaded in the cup 23, the rotor 3 is thus held centered in the housing and is rotatable about the central axis of the housing. To facilitate the rotation of the rotor, a ring 41 and hemispherical pad 43 of low coefficient of friction material, such as TEFLON, are provided in the groove 35 and recess 37, respectively.

The means 13 for rotating the rotor 3 comprises an inlet port 45 for the housing for directing fluid, such as air, under pressure from a source thereof (not shown) against the vanes 19 at an angle causing the rotor to rotate. The handle 9 has a coupling 46 at its end adapted to be secured to the source of air under pressure and passaging indicated at 47 for providing communication from the source of air under pressure to the inlet port 45. The rotor 3 is rotated at a relatively high speed by the air under pressure to expel, by centrifugal force, saliva, water, or other flowable material, such as enamel chips and drilling dust, which may come into contact with the reflective surface 5 of the rotor during the dental procedure, thereby keeping it clean. The rotating means 13 further comprises an outlet port 49 for the cup for venting the air introduced into the cup 23, the air flowing from the cup via passaging, indicated at 51, in the handle in communication with the outlet port. This venting arrangement together with the seal formed between the ridge 33 on the disc 17 and the ring 35 prevent the area of the oral cavity to be viewed from being exposed to the air under pressure.

Disassembly of the ring and cup for enabling the replacement of the rotor when its bearing surfaces are worn or its reflective surface 5 is marred is effected by turning the ring 25 relative to the cup 23 via the use of a pair of specially designed tools generally indicated at 53 in FIG. 4. The ring has a series of recesses 55 at spaced intervals therearound adapted to receive complementary shaped projections 57 on a first or upper tool 53A of the pair of tools, and the cup 23 has a plurality of recesses 59 in its outer surface adapted to receive complementary shaped projections 61 on the other or lower tool 53B of the pair. To disassemble the housing, the dentist or his assistant holds the tools 53, one in each hand, moves them into mating relationship with the ring 25 and cup 23, and turns the upper tool relative to the lower tool to remove the ring from the cup. Assembly of the housing is effected by turning the tools relative to each other in the opposite direction.

As will be observed from the foregoing, the mirror of this invetion is thus self-cleaning in operation, relatively compact, safe to use, may be readily sterilized, and does not introduce fluid under pressure (air) into the oral cavity in the area to be viewed. Moreover, the rotor, being relatively inexpensive, may be readily replaced whenever its bearing surfaces become worn or its reflective surface becomes marred.

While the reflective surface 5 of the rotor 3 is shown as being supported at an acute angle to the longitudinal axis of the handle 9, it is contemplated that it may be supported at any angle relative to the axis of the handle including an obtuse angle. Moreover, it is contemplated that the rotor 3, which is shown and described as being of one-piece construction, may comprise two or more pieces secured together, and the low coefficient of friction material, which is shown and described as being in the form of separate and discrete pieces (e.g., ring 41 and pad 43), may be in the form of a coating on the ridge 33 and the recess 37 of the rotor. In addition, while the rotor 3 is described as being formed of synthetic plastic material, it is contemplated that it may be made of other suitable material, such as stainless steel, which can withstand sterilizing temperatures in an autoclave. Lastly, it is contemplated that the mirror 1 may be used for other applications, such as a surgical procedure, in which the mirror may be exposed to a flowable material which would render its reflective surface wholly or partially non-reflective.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A self-cleaning mirror for use in dental and surgical procedures comprising:
    a generally cup-shaped housing having an open mouth;
    a handle connected to the housing;
    a unitary rotor in the housing comprising a shaft, a disc at one end of the shaft, and vanes spaced at intervals around the shaft;
    means at the center of the bottom of the housing engaged by the other end of the shaft for centering the shaft at its other end in the housing, with the other end of the shaft rotatable on said means and freely axially disengageable from said means;
    a ring for retaining the rotor in the housing with the rotor centered in the housing, said ring being removably threaded in the open mouth of the housing and engaging the disc at the periphery of the disc for holding the rotor in the housing centered therein;
    the outside face of the disc being mirrorized;
    the housing having a peripheral inlet for entry of fluid under pressure from a source thereof with the fluid directed against the vanes, and a peripheral outlet for venting fluid from the spaces between the vanes, for rotating the rotor in the housing;
    the ring being removable for drop-out of the rotor from the housing and the rotor being replaceable in the housing, centering itself for interengagement of the said other end of the shaft and said centering means at the center of the bottom, and becoming centered at its periphery on threading the ring back onto the housing and resultant engagement of the ring with the periphery of the disc.

2. A self-cleaning mirror as set forth in claim 1 having low coefficient of friction material between said other end of the shaft and said means at the bottom of the housing and between said ring and the periphery of the disc.

3. A self-cleaning mirror as set forth in claim 1 wherein said means at the bottom of the housing comprises a boss on the bottom of the housing having a hemispherical end and the said other end of the shaft has a hemispherical recess receiving the hemispherical end of the boss.

4. A self-cleaning mirror as set forth in claim 1 wherein the disc, adjacent its periphery, and the ring have interengaging annular tongue and groove means for holding the disc centered.

5. A self-cleaning mirror as set forth in claim 1 wherein said means at the bottom of the housing comprises a boss on the bottom of the housing having a hemispherical end and the said other end of the shaft has a hemispherical recess receiving the hemispherical end of the boss and wherein the disc, adjacent its periphery, and the ring have interengaging annular tongue and groove means for holding the disc centered.

6. A self-cleaning mirror as set forth in claim 5 wherein the groove is in the bottom of the ring and the tongue is on the outside face of the disc and the periphery of the disc.

7. A self-cleaning mirror as set forth in claim 6 having low coefficient of friction material coatings for reducing friction between the boss and the shaft and between the tongue and groove.

8. A self-cleaning mirror as set forth in claim 6 wherein the ring has a series of recesses in its outer face at spaced intervals therearound adapted to receive complementary shaped projections on a first tool of a pair of tools, and said housing member has a plurality of recesses in its outer surface adapted to receive complementary shaped projections on the second tool of the pair, whereby by turning said tools relative to each other the ring may be threaded onto and off of said housing member.

9. A self-cleaning mirror as set forth in claim 1 wherein the handle has fluid passages therein in communication with said inlet and outlet.

* * * * *